United States Patent [19]

Dennison

[11] Patent Number: 4,923,058
[45] Date of Patent: May 8, 1990

[54] CONTAINER FOR STORING AND DISPLAYING BABY TEETH

[76] Inventor: Mary R. Dennison, 945 Dovington Dr., Hoffman Estates, Ill. 60194

[21] Appl. No.: 358,582

[22] Filed: May 30, 1989

[51] Int. Cl.⁵ .............................................. B65D 85/00
[52] U.S. Cl. ..................................... 206/83; 206/564; 217/25.5
[58] Field of Search ................. 206/83, 561, 562, 563, 206/564, 565, 566, 373; 220/21, 20; 217/6, 25.5, 26; 433/26, 77, 79

[56] References Cited

U.S. PATENT DOCUMENTS 4,694,956  9/1987  Sims ..................................... 206/83
4,775,318  10/1988  Breslin ................................. 433/26

Primary Examiner—Paul T. Sewell
Assistant Examiner—Jacob K. Ackun, Jr.
Attorney, Agent, or Firm—Leydig, Voit & Mayer

[57] ABSTRACT

A container includes a hollow body and a hinged cover. An insert in the body is formed with twenty upwardly opening pockets for receiving a set of twenty baby teeth. The pockets are sized in accordance with the size of the different types of teeth. In addition, the pockets are arranged such that, when the teeth are stored, their placement assimilates the placement of the teeth in the upper and lower jaws.

15 Claims, 1 Drawing Sheet

U.S. Patent
May 8, 1990
4,923,058
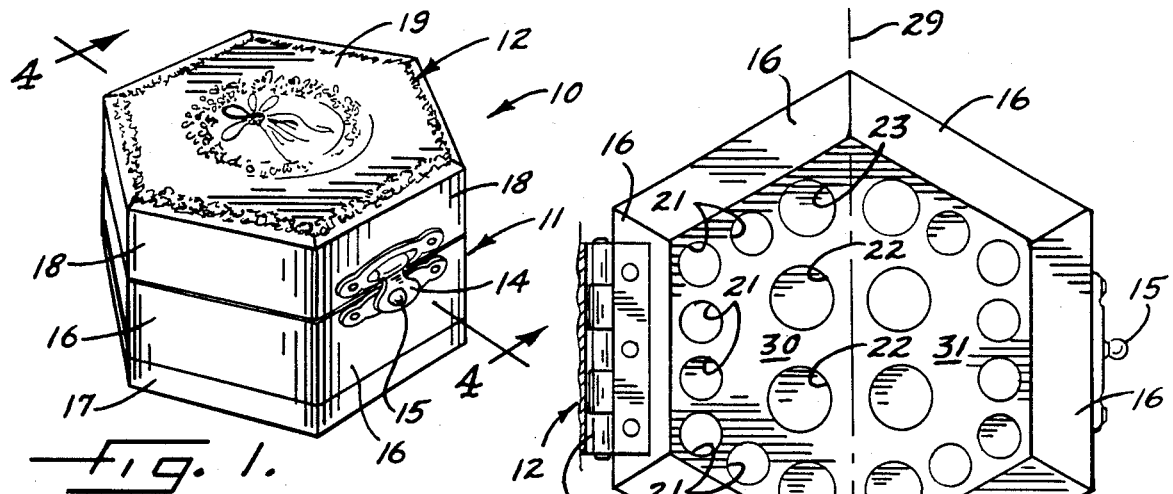
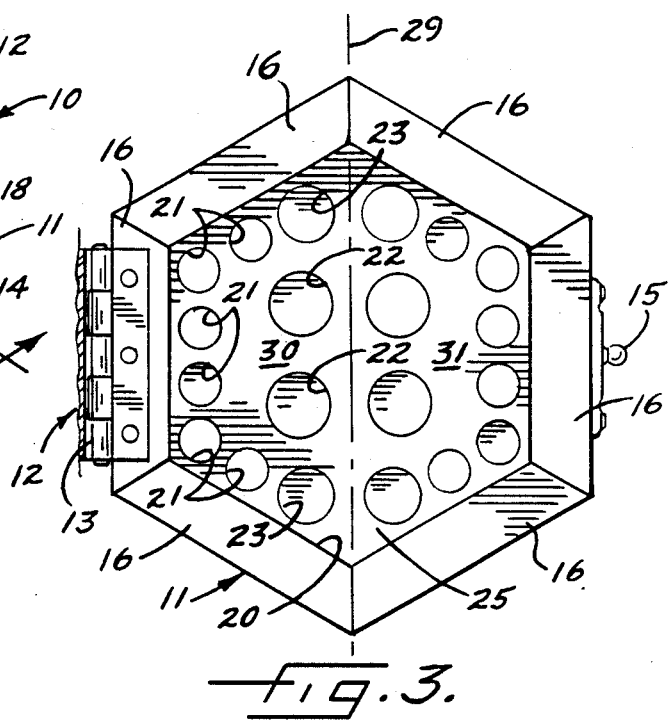
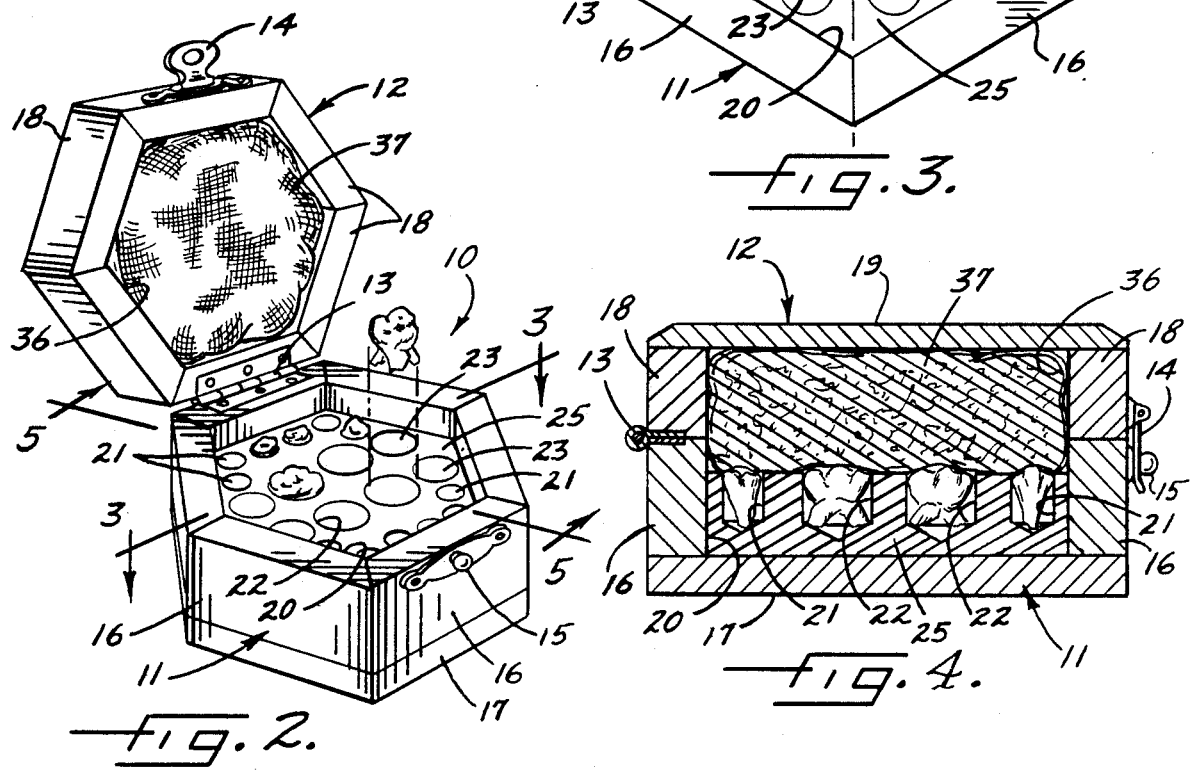
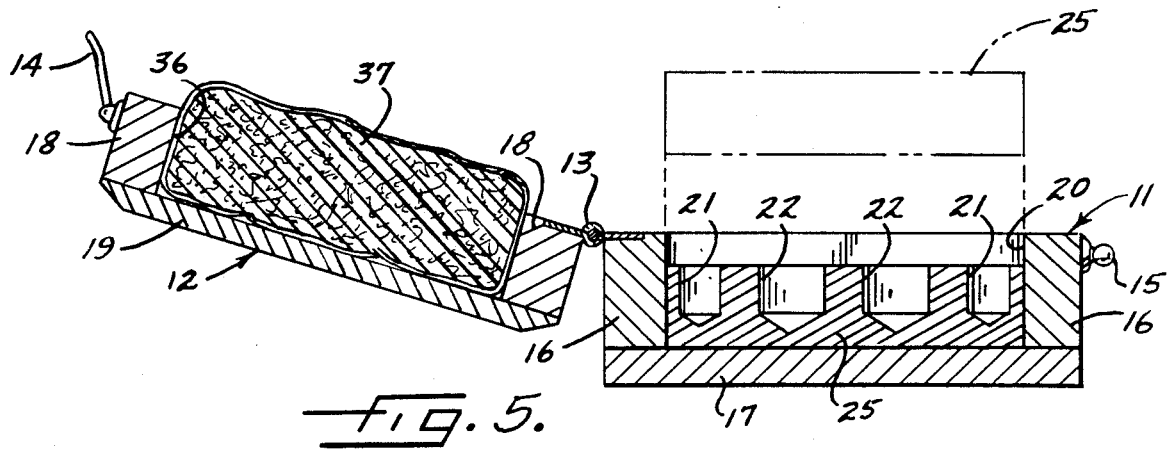

CONTAINER FOR STORING AND DISPLAYING BABY TEETH

BACKGROUND OF THE INVENTION

This invention relates generally to a container and, more particularly, to a container for storing a child's baby teeth so that the teeth may be retained as a keepsake.

Many parents like to keep their children's baby teeth as a remembrance. Often the teeth are stored rather slipshod in a spare container which was originally designed and used for another purpose. A need exists for a container which is specifically arranged for baby teeth.

SUMMARY OF THE INVENTION

The general aim of the present invention is to provide a new and improved container for storing and displaying baby teeth, the container being particularly characterized in that it holds the teeth in a pattern which is generally similar to the placement of the teeth in the mouth.

A more detailed object of the invention is to achieve the foregoing by providing a container having twenty upwardly opening pockets for receiving a corresponding number of baby teeth. The pockets are tailored in size to the size of the different types of teeth and are geometrically arranged similar to the arrangement of the teeth around the jaw.

The invention also resides in the unique construction of the body and cover of the container and in the provision of a base for holding the teeth and adapted to be inserted into the container body.

These and other objects and advantages of the invention will become more apparent from the following detailed description when taken in conjunction with the accompanying drawings

BRIEF DESCRIPTION OF THE DRAWINGS

FIG. 1 is a perspective view of a new and improved baby tooth container incorporating the unique features of the present invention, the cover of the container being shown in a closed position.

FIG. 2 is a view similar to FIG. 1 but shows the cover in a partially open position.

FIG. 3 is an enlarged top plan view of the body of the container as seen in the direction of the arrows 3—3 of FIG. 2, the cover of the container being broken away.

FIG. 4 is an enlarged cross-section taken substantially in a vertical plane which contains the line 4—4 of FIG. 1.

FIG. 5 is an enlarged cross-section taken substantially in a vertical plane which contains the line 5—5 of FIG. 2, the cover being shown in a fully open position.

DETAILED DESCRIPTION OF THE PREFERRED EMBODIMENT

For purposes of illustration, the invention has been shown in the drawings as being embodied in a container 10 having an upwardly opening hollow body 11 and having a cover 12 hinged thereto. While the body and cover may take various configurations, they preferably are shaped as regular hexagons and have identical outer peripheral dimensions. A hinge 13 extends along one side of the body and the cover and supports the cover for swinging upwardly and downwardly between open and closed positions about a predetermined axis. The opposite side of the cover carries a hinged catch 14 which coacts with a strike 15 on the body to latch the cover releasably in its closed position.

The body 11 and the cover 12 may be molded of plastic. For the sake of appearance and quality, however, the body and the cover preferably are fabricated of wood. Thus, the body 11 includes six wood strips 16 which are cemented in end-to-end relation. A bottom 17 (FIGS. 4 and 5) made of wood underlies the strips 16 and is cemented thereto. Similarly, the cover 12 includes six end-to-end wood strips 18 and a wood top 19.

In accordance with the present invention, the body 11 includes a recess 20 which contains twenty pockets 21, 22 and 23 for holding baby teeth. Various pockets are sized in accordance with the size of various types of teeth, and the pockets are arranged to generally assimilate the arrangement of the teeth in the upper and lower jaws.

In this particular instance, the recess 20 also is in the shape of a regular hexagon and its sides are defined by the inner sides of the wood strips 16 of the body 11. The pockets 21, 22 and 23 are in the form of drilled holes. Advantageously, the pockets are drilled in a separate wood insert or base 25 whose exterior periphery is shaped as a regular hexagon. The base is sized to telescope snugly into the recess 20 in the body 11 and rests on the upper side of the bottom 17 of the body. By virtue of the insertable base 25, the body may be fabricated of attractive wood and at a lower cost then would be possible without the base.

In carrying out the invention, the pockets 21, 22 and 23 are arranged in groups of ten pockets each, the two groups of pockets assimilating the placement of the teeth of the upper and lower jaws, respectively. As shown in FIG. 3, the body includes a transverse centerline 29 extending between diametrically opposite apices of the hex. Such centerline extends parallel to the axis of the hinge 13 and divides the base 25 into two imaginary sections 30 and 31 (FIG. 2) which are mirror images of one another Ten pockets 21, 22 and 23 are located in each of the aforementioned sections 30, 31 of the base 25. Each section includes six small-diameter pockets 21, two large-diameter pockets 22 and two intermediate pockets 23. The small pockets 21 are adapted to hold the incisors and canines, the large pockets 22 are adapted to hold the second molars and the intermediate pockets 23 are adapted to hold the first molars.

As shown most clearly in FIG. 3, the ten pockets 21, 22 and 23 of each section 30, 31 of the base 25 are arranged so as to define the two bases and two sides of an isosceles trapezoid having its long base extending parallel to and located adjacent the centerline 29. Thus, the long base of the trapezoid is defined by the two large pockets 22 and the two intermediate pockets 23, the large pockets 22 being located between the intermediate pockets 23. The short base of the trapezoid is defined by four of the small pockets 21. One of the remaining small pockets 21 defines one side of the trapezoid while the final small pocket 21 defines the other side of the trapezoid.

When the proper teeth are placed in the ten pockets 21, 22 and 23 of each section 30, 31 of the base 25, the teeth are arranged in a manner assimilating the placement of the teeth in one jaw. The pockets in the other section are arranged as a mirror image of the pockets in the first section and thus assimilate the placement of the teeth in the other jaw. Accordingly, the teeth may be logically arranged in and realistically displayed by the container 10.

The cover 12 is formed with a downwardly opening hexagonal recess 36 which snugly receives a fabric cushion 37. When the cover is closed, the cushion rests on any teeth which project upwardly from the base 25. When the cover is open, the cushion enhances and softens the appearance of the cover.

From the foregoing, it will be apparent that the present invention brings to the art a new and improved container 10 which enables baby teeth to be stored as keepsakes. Because of the arrangement and size of the pockets 21, 22 and 23, the teeth may be logically stored and realistically displayed.

I claim:

1. A container for storing baby teeth, said container comprising a base having a substantially flat and planar upper surface, and twenty upwardly opening pockets in said base for receiving and storing baby teeth, twelve of said pockets having a small transverse dimension for receiving incisors and canines, four of said pockets having a large transverse dimension for receiving second molars, and four of said pockets having an intermediate transverse dimension for receiving first molars, said base being a unitary member having a transverse centerline dividing the base into first and second sections which are mirror images of one another, each of said sections having six small pockets, two large pockets and two intermediate pockets.

2. A container as defined in claim 1 in which four of the small pockets of each section lie along a first straight line extending substantially parallel to said centerline, and the two large pockets and the two intermediate pockets of each section lying along a second straight line located between and extending parallel to said first straight line and said centerline.

3. A container as defined in claim 2 in which the two large pockets of each section are located between the two intermediate pockets thereof, said two large pockets and said two intermediate pockets defining the long base of an isosceles trapezoid, said four pockets of each section defining the short base of said trapezoid, one remaining small pocket of each section lying along one side of said trapezoid, and the final small pocket of each section lying along the other side of said trapezoid.

4. A container as defined in claim 3 in which each section of said base defines an isosceles trapezoid larger than and substantially congruent with the trapezoid defined by the pockets in said section.

5. A container as defined in claim 4 in which said container further includes a body having an upwardly opening recess of the same peripheral shape as the outer periphery of said base, said base being telescoped into said recess.

6. A container as defined in claim 1 in which said container further includes a body having an upwardly opening recess of the same peripheral shape as the outer periphery of said base, said base being telescoped into said recess.

7. A container for storing baby teeth, said container comprising a body having an upwardly opening recess and having means within said recess defining twenty upwardly opening pockets for storing baby teeth, said recess having a transverse centerline dividing the body into first and second sections which are mirror images of one another, there being ten pockets in each section with the pockets of each section being arranged so as to be a mirror image of the pockets of the other section, and the pockets of each section defining a geometrical figure which generally assimilates the geometrical figure defined by the teeth in a human jaw, and a top cover selectively movable between positions opening and closing said recess, said cover exposing the upper ends of all of said pockets when said cover is open.

8. A container as defined in claim 7 in which said cover is hinged to said body to swing upwardly from and downwardly to a closed position relative to said recess about an axis extending parallel to said centerline.

9. A container for storing baby teeth, said container comprising a body having an upwardly opening recess in the shape of a regular hexagon and having means within said recess defining upwardly opening pockets for storing baby teeth, said recess having a transverse centerline extending between diametrically opposite apices of the recess and dividing the recess into first and second sections which are mirror images of one another, there being ten pockets in each section with the pockets of each section being arranged so as to be a mirror image of the pockets of the other section, six of the pockets of each section having a small transverse dimension for receiving incisors and canines, two of the pockets of each section having a large transverse dimension for receiving second molars, and two of the pockets of each section having an intermediate transverse dimension for receiving first molars, the pockets in each section being located so as to define an isosceles trapezoid within said recess, the large and the intermediate pockets of each section defining the long base of the trapezoid, four of the small pockets of each section defining the short base of the trapezoid, one of the remaining small pockets of each section defining one side of the trapezoid, and the final small pocket of each section defining the other size of the trapezoid.

10. A container as defined in claim 9 in which the two large pockets of each section are located between the two intermediate pockets thereof.

11. A container as defined in claim 10 in which the long base of said trapezoid extends parallel to and is located adjacent said centerline.

12. A container as defined in claim 11 in which the outer periphery of said body defines a regular hexagon.

13. A container as defined in claim 12 further including a base of substantially the same size and shape as said recess and telescoped into said recess, said pockets being formed in said base.

14. A container as defined in claim 13 further including a cover attached to said body to swing between open and closed positions relative to said recess about an axis extending parallel to said centerline, said cover having an outer periphery defining a regular hexagon which, when said cover is in said closed position, is superimposed on the hexagon defined by the outer periphery of said body.

15. A container as defined in claim 14 in which said cover is formed with a downwardly opening recess, and a cushion telescoped snugly in said recess.

* * * * *